United States Patent
Frodyma

(10) Patent No.: US 9,193,940 B2
(45) Date of Patent: *Nov. 24, 2015

(54) BACTERIA CULTURES AND COMPOSITIONS COMPRISING BACTERIA CULTURES

(71) Applicant: NOVOZYMES BIOLOGICALS, INC., Salem, VA (US)

(72) Inventor: Michael Eric Frodyma, Saskatchewan (CA)

(73) Assignee: NOVOZYMES BIOLOGICALS, INC., Salem, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/096,124

(22) Filed: Dec. 4, 2013

(65) Prior Publication Data

US 2014/0106438 A1 Apr. 17, 2014

Related U.S. Application Data

(63) Continuation of application No. 13/751,411, filed on Jan. 28, 2013, now Pat. No. 8,628,765, which is a continuation of application No. 12/374,361, filed as application No. PCT/US2007/075185 on Aug. 3, 2007, now Pat. No. 8,383,097.

(60) Provisional application No. 60/837,065, filed on Aug. 11, 2006, provisional application No. 60/891,279, filed on Feb. 23, 2007.

(51) Int. Cl.
| | |
|---|---|
| *D06M 16/00* | (2006.01) |
| *C11D 3/38* | (2006.01) |
| *C11D 3/00* | (2006.01) |
| *C11D 3/386* | (2006.01) |
| *C11D 11/00* | (2006.01) |
| *C12N 1/20* | (2006.01) |

(52) U.S. Cl.
CPC .............. *C11D 3/381* (2013.01); *C11D 3/0031* (2013.01); *C11D 3/386* (2013.01); *C11D 3/38618* (2013.01); *C11D 3/38627* (2013.01); *C11D 3/38636* (2013.01); *C11D 3/38645* (2013.01); *C11D 3/38654* (2013.01); *C11D 11/0017* (2013.01); *C11D 11/0023* (2013.01); *C12N 1/20* (2013.01)

(58) Field of Classification Search
None
See application file for complete search history.

(56) References Cited

U.S. PATENT DOCUMENTS

| | | | |
|---|---|---|---|
| 5,811,287 A | 9/1998 | Aoshima | |
| 5,821,112 A | 10/1998 | Botto | |
| 6,376,451 B1 | 4/2002 | Teasdale | |
| 6,610,642 B2 | 8/2003 | Ghosh | |
| 6,927,055 B2 | 8/2005 | Poulose | |
| 8,409,591 B2 | 4/2013 | Farmer | |
| 2002/0128167 A1 | 9/2002 | Ghosh | |
| 2003/0089381 A1 | 5/2003 | Manning, Jr. | |
| 2011/0274676 A1 | 11/2011 | Farmer | |

FOREIGN PATENT DOCUMENTS

| | | |
|---|---|---|
| CN | 101575807 | 11/2009 |
| CN | 102115697 | 7/2011 |
| JP | 10249388 | 9/1998 |
| JP | 2001-299328 A | 10/2001 |
| JP | 2002161481 | 6/2002 |
| JP | 2002-226893 A | 8/2002 |
| JP | 2003253299 | 9/2003 |
| JP | 2006-104257 A | 4/2006 |
| WO | 96/34108 A2 | 10/1996 |
| WO | 99/20726 A1 | 4/1999 |
| WO | 00/03752 A1 | 1/2000 |
| WO | 00/34450 A1 | 6/2000 |
| WO | 00/61201 A1 | 10/2000 |
| WO | 01/11354 A1 | 2/2001 |
| WO | 01/13927 A2 | 3/2001 |
| WO | 02/33035 A1 | 4/2002 |
| WO | 02/066591 A1 | 8/2002 |
| WO | 03/064755 A2 | 8/2003 |
| WO | 03/099987 A1 | 12/2003 |
| WO | 03/104376 A1 | 12/2003 |
| WO | 2008/021761 A2 | 2/2008 |
| WO | 2008/118749 A2 | 10/2008 |
| WO | 2009/148800 A1 | 12/2009 |
| WO | 2010/006235 A1 | 1/2010 |
| WO | 2010/014715 A1 | 2/2010 |
| WO | 2011/163500 A2 | 12/2011 |

OTHER PUBLICATIONS

Gupta et al, 2002, Appl Microbiol Biotechnol 59, 15-32.
Ruiz-Garcia et al., International Journal of Systematic Evolutionary Micriobiology, vol. 55, No. 1, pp. 191-195 (2005).
Gao et al., Journal of Applied Polymer Science, vol. 117, No. 5, pp. 3075-3082 (2010).
Munk et al., Journal of Surfactants and Detergents, vol. 3, No. 4, pp. 505-515 (2000).
Munk et al., Journal of Surfactants and Detergents, vol. 4, No. 4, pp. 385-394 (2001).
Nagoh et al., Tenside Surf. Det., vol. 42, No. 1, pp. 7-12 (2005).
Novozymes, Carpet Ease Spot product sheet (2010).
Novozymes, Freshen Free product sheet (2011).
Obendorf, AATCC Review, vol. 4, No. 1, pp. 17-23 (2004).

*Primary Examiner* — Kade Ariani

(74) *Attorney, Agent, or Firm* — Elias Lambiris

(57) ABSTRACT

The present invention relates to bacteria cultures and composition comprising one or more cultures of the invention. The invention also relates to methods of washing or cleaning laundry or fabrics and surfaces as well as degrading waste material using a bacteria culture of the invention.

20 Claims, No Drawings

BACTERIA CULTURES AND COMPOSITIONS COMPRISING BACTERIA CULTURES

CROSS-REFERENCE TO RELATED APPLICATIONS

This application is a continuation of U.S. application Ser. No. 13/751,411 filed Jan. 28, 2013 (now U.S. Pat. No. 8,628,765), which is a continuation of U.S. application Ser. No. 12/374,361 filed Jan. 19, 2009 (now U.S. Pat. No. 8,383,097) which is a 35 U.S.C. 371 national application of PCT/US2007/075185 filed Aug. 3, 2007, which claims priority or the benefit under 35 U.S.C. 119 of U.S. provisional application Nos. 60/837,065 and 60/891,279 filed Aug. 11, 2006 and Feb. 23, 2007, respectively, the contents of which are fully incorporated herein by reference.

FIELD OF THE INVENTION

The present invention relates to isolated bacteria cultures and compositions comprising said cultures. A composition of the invention may advantageously be used for washing, especially laundry or newly manufactured fabrics, cleaning of surfaces, such as carpets, cleaning of drains and septic tanks, as well as degrading waste material.

BACKGROUND

Compositions for washing laundry often contain surfactants and other active ingredients such as enzymes for removing stubborn stains. Enzymes may not be able to remove all kinds of complex strains.

WO 03/099987 discloses an article and method of cleaning fabric, wherein soiled fabric is soaked in water in the presence of an article containing one or more harmless microorganisms capable of excreting enzymes useful for cleaning.

Even though a huge number of composition and cleaning systems are known in the art there is never the less still a desire for compositions which exhibit strong washing and cleaning capabilities. There is still a continuing need for providing efficient compositions for washing and cleaning of laundry, fabrics and surfaces.

SUMMARY OF THE INVENTION

The present invention relates to compositions comprising selected whole bacteria cultures. The bacteria are isolated from their natural environment. The composition of the invention may be used for washing especially laundry and newly manufactured fabrics and cleaning surfaces such as carpets. A composition of the invention may optionally be supplemented with surfactants and/or other active ingredients, such as enzymes.

It has been found that selected (whole) bacteria cultures of the invention have washing and cleaning benefits when used for washing laundry and fabrics and/or cleaning surfaces. More specifically the inventors found that the bacteria cultures of the invention derived from strains of the genus *Bacillus*, preferably strains of the species *Bacillus subtilis*, *Bacillus amyloliquefaciens*, *Bacillus simplex*, *Bacillus velezensis*, and *Bacillus atrophaeus*, and compositions containing one or more bacteria cultures of the invention, have strong wash performance and cleaning efficacy.

In the first aspect the invention relates to bacteria cultures having characteristics substantially identical to that of a strain selected from the group consisting of:

the strain having the deposit accession number PTA-7541;
the strain having the deposit accession number PTA-7542;
the strain having the deposit accession number PTA-7543;
the strain having the deposit accession number PTA-7544;
the strain having the deposit accession number PTA-7545;
the strain having the deposit accession number PTA-7546;
the strain having the deposit accession number PTA-7547;
the strain having the deposit accession number PTA-7548;
the strain having the deposit accession number PTA-7549.
the strain having the deposit accession number PTA-7550,
the strain having the deposit accession number PTA-7789,
the strain having the deposit accession number PTA-7790,
the strain having the deposit accession number PTA-7791,
the strain having the deposit accession number PTA-7792,
the strain having the deposit accession number PTA-7793,
or, a mixture of two or more of the strains.

In a second aspect the invention relates to a composition comprising one or more biologically active cultures of the invention. In a preferred embodiment the composition also contains one or more ingredients, including surfactants, hydrotropes, preservatives, fillers, builders, stabilizer, fragrances, anti-redeposition agents, nutrients, biostimulants, and enzymes; or a combination of one or more thereof.

In other aspects the invention relates to methods of washing and cleaning fabrics and surfaces, respectively, comprising subjecting said objects to a bacteria culture or composition of the invention. The invention also relates to degrading waste material using a culture or composition of the invention.

In context of the invention soils/stains especially contemplated include blood, butterfat, cooking oil, sebum, and ballast. The term "ballast" is an art-recognized term for a general "soil" containing chocolate, blood, red wine, and milk mixed together. Other soils/stains contemplated include (e.g., pork) lard, (e.g., hamburger) oil, (e.g., hamburger) grease.

DETAILED DESCRIPTION OF THE INVENTION

The present invention relates to isolated (whole) bacteria cultures and compositions comprising one or more of said cultures. The cultures and compositions may be used for various washing and cleaning purposes, especially laundry and fabric washing as well as surface cleaning. Other uses, including waste degradation, are also contemplated.

Cultures of the Invention

In the first aspect the invention relates to bacteria cultures having characteristics substantially identical to that of a strain selected from the group consisting of:

the strain having the deposit accession number PTA-7541;
the strain having the deposit accession number PTA-7542;
the strain having the deposit accession number PTA-7543;
the strain having the deposit accession number PTA-7544;
the strain having the deposit accession number PTA-7545;
the strain having the deposit accession number PTA-7546;
the strain having the deposit accession number PTA-7547;
the strain having the deposit accession number PTA-7548;
the strain having the deposit accession number PTA-7549.
the strain having the deposit accession number PTA-7550,
the strain having the deposit accession number PTA-7789,
the strain having the deposit accession number PTA-7790,
the strain having the deposit accession number PTA-7791,
the strain having the deposit accession number PTA-7792,
the strain having the deposit accession number PTA-7793,
or, a mixture of two or more of the strains.

In a preferred embodiment a culture of the invention has properties identical to one of above mentioned deposited strains, or a mixture thereof. The culture may preferably be one or more of the above mentioned deposited strains. A culture of the invention may be a progeny of one of the deposited strains. A culture of the invention is preferably substantially pure, such as at least 90% pure, preferably at least 95% pure, more preferably at least 97% pure, even more preferably at least 99% pure.

The deposited bacteria cultures are derived from isolated naturally occurring bacteria strains. All strains were collected in the United States in 2005. Cultures of the invention may consist of dormant bacteria spores and/or viable bacteria.

A culture of the invention having substantially identical characteristics of one or more of the deposited strains may be derived from any bacteria, preferably from strains of the genus *Bacillus*, especially strains derived from species selected from the group consisting of *Bacillus subtilis, Bacillus amyloliquefaciens, Bacillus simplex, Bacillus velezensis*, and *Bacillus atrophaeus*.

Above mentioned deposited strains were deposited on 20 Apr. 2006 and 18 Aug. 2006, as indicated in more details below in the "Materials & Methods"-section, under terms of the Budapest Treaty on the International Recognition of the Deposit of Microorganisms for the Purposes of Patent Procedure at American Type Culture Collection (ATCC), P.O. Box 1549, Manassas, Va. 20108, USA.

In embodiments of the invention two or more bacteria cultures of the invention are combined. Preferred combinations include deposited strains PTA-7547 and PTA-7548 which, as indicated below, are suitable for surface cleaning, especially carpet cleaning.

Composition of the Invention

In the second aspect the invention relates to a composition comprising one or more cultures of the invention.

A composition of the invention has a number of potential advantages over for instance, traditional enzymatic washing and/or cleaning compositions as, e.g., laundry and/or other soiled objects with complex and/or stubborn stains in general require multi-enzyme washing or cleaning systems. Compositions of the invention comprise one or more bacteria cultures of the invention having at their disposal the entire metabolic potential of the bacteria culture, or a combination of one or more cultures. Due to the cost of preparing effective multienzyme compositions, adding a bacteria culture as an active stain removing ingredient may be a good and/or cost efficient alternative to compositions comprising, e.g., mono-component enzymes. A bacterial culture of the invention may also advantageously be used to at least partly substitute enzymes in washing or cleaning compositions. In an embodiment the composition comprises from 0.1-90 wt-% culture, preferably 0.5-50 wt.-% culture, especially from 1-10 wt-% culture of the invention.

In a preferred embodiment a composition of the invention also contains one or more surfactants and/or optionally other active ingredients, such as enzymes. A composition of the invention may be in solid or liquid form. The composition may be a concentrate to be diluted, rehydrated and/or dissolved in a solvent, including water, before use. The composition may also be a ready-to-use (in-use) composition. The composition may furthermore be an active cleaning base ingredient to be incorporated into other cleaning or washing compositions.

Other contemplated ingredients include surfactants, hydrotropes, preservatives, fillers, builders, complexing agents, polymers, stabilizers, perfumes, biostimulants or nutrients, conventional detergent ingredients, and enzymes, or combinations of one or more thereof.

Surfactants

The surfactants may be non-ionic including semi-polar and/or anionic and/or cationic and/or zwitterionic. The surfactant(s) should cause as little harm to the bacteria culture's activity as possible.

The surfactants may be present in a composition of the invention at a level of from 0.1% to 60% by weight.

In one embodiment the composition contains from about 1% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid or soap.

In an embodiment the composition contains from about 0.2% to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl N-alkyl derivatives of glucosamine ("glucamides").

Hydrotropes

The composition may contain hydrotropes. The term "hydrotrope" generally means a compound with the ability to increase the solubilities, preferably aqueous solubilities, of certain slightly soluble organic compounds. Examples of hydrotropes include sodium xylene sulfonate (SXS) and sodium cumene sulfonate (SCS).

Metal Chelation Agents

The composition may contain a metal chelating agent such as carbonates, bicarbonates, and sesquicarbonates.

Solvents

The composition may comprise a solvent such as water or an organic solvent such as isopropyl alcohol or a glycol ether.

Builders or Complexing Agents

The composition may also contain 0-65% of a builder or complexing agent such as zeolite, phosphates, such as diphosphate, triphosphate, phosphonate, carbonate, citrate, nitrilotriacetic acid, ethylenediaminetetraacetic acid, diethylenetriaminepentaacetic acid, alkyl- or alkenylsuccinic acid, silicates, such as soluble silicates, metasilicates, layered silicates (e.g. SKS-6 from Hoechst).

Polymers

The composition may comprise one or more polymers. Examples are carboxymethylcellulose, poly(vinylpyrrolidone), poly(ethylene glycol), poly(vinyl alcohol), poly(vinylpyridine-N-oxide), poly(vinylimidazole), polycarboxylates such as polyacrylates, maleic/acrylic acid copolymers and lauryl methacrylate/acrylic acid copolymers.

Stabilizers

If an enzyme(s) is(are) present in the composition it(they) may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in e.g. WO 92/19709 and WO 92/19708.

Detergent Ingredients

The composition may also contain other conventional detergent ingredients such as, e.g. fabric conditioners including clays, foam boosters, suds suppressors, anti-corrosion agents, soil-suspending agents, anti-soil redeposition agents, dyes, bactericides, optical brighteners, hydrotropes, tarnish inhibitors, or perfumes.

In an embodiment the solid composition contains the following constitutes: hydrotropes, anionic or nonionic surfactants, builders, carbonates for pH control and metal chelation, solvents, fillers, dye, perfume, and fluorescent whitening agent.

Cleaning Compositions Suitable for Surface Cleaning

The bacterial cultures of the invention may be used in a composition suitable for cleaning surfaces, such as hard and soft surfaces, such as especially carpets and the like. Examples of hard and soft surfaces are mentioned below.

In a preferred embodiment a bacteria culture of the invention or a combination of two or more cultures are used in a surface cleaning composition comprising a surfactant system or cleaning composition. In a preferred embodiment the composition is a carpet cleaner composition, i.e., a carpet cleaning composition comprising a surfactant system or cleaning composition, e.g., a surfactant system or cleaning composition disclosed in WO 2007/076337 (which is hereby incorporated by reference). The carpet cleaner may be a carpet extraction cleaner or a carpet spot remover.

In one embodiment said surfactant system comprises two or more nonionic surfactants and an anionic surfactant. In an embodiment one of the nonionic surfactants is a water insoluble nonionic surfactant. Further, in another embodiment the surfactant system comprises two or more water soluble nonionic surfactants and one water insoluble nonionic surfactant. Further, the surfactant system may also comprise one water soluble anionic surfactant, one water-soluble nonionic surfactant and one water insoluble nonionic surfactant.

The ratio between anionic surfactant(s) and nonionic surfactant(s) may in a preferred embodiment be between 10:1 and 1:10, preferably between 10:1 and 1:1, more preferably between 8:1 and 1:1, even more preferably between 6:1 and 1:1.

In an embodiment of the invention the cleaning composition is formulated as follows:

| COMPONENT | PERCENT BY WEIGHT |
| --- | --- |
| Solvent | 50-95 |
| Anionic surfactant. | 2.5-15 |
| Water insoluble nonionic surfactant | 2.5-15 |
| Buffer salts | 0.25-1 |
| Bacteria Culture of the invention | $10^5$-$10^9$ cfu/ml cleaning composition |
| Optionally other ingredients | 0.1-10 |

The surfactants (including ratio between surfactants), solvents, salts, and optional ingredients (such as enzymes) may be any mentioned above or below.

Anionic Surfactants

The anionic surfactant(s) may be water soluble anionic surfactants and/or water insoluble anionic surfactants. Water soluble anionic surfactants are preferred.

Examples of suitable water soluble anionic surfactants include those selected from the group consisting of alkyl sulfates, alkyl ether sulfates, alkyl amido ether sulfates, alkyl aryl polyether sulfates, alkyl aryl sulfates, alkyl aryl sulfonates, monoglyceride sulfates, alkyl sulfonates, alkyl amide sulfonates, alkyl aryl sulfonates, benzene sulfonates, toluene sulfonates, xylene sulfonates, cumene sulfonates, alkyl benzene sulfonates, alkyl diphenyloxide sulfonate, alpha-olefin sulfonates, alkyl naphthalene sulfonates, paraffin sulfonates, lignin sulfonates, alkyl sulfosuccinates, ethoxylated sulfosuccinates, alkyl ether sulfosuccinates, alkylamide sulfosuccinates, alkyl sulfosuccinamate, alkyl sulfoacetates, alkyl phosphates, phosphate ester, alkyl ether phosphates, acyl sarconsinates, acyl isethionates, N-acyl taurates, N-acyl-N-alkyltaurates, and alkyl carboxylates.

Examples of preferred water soluble anionic surfactants include sodium dodecyl sulfate (sodium lauryl sulfate), sodium laureth sulfate (sodium lauryl ether sulfate), sodium dodecyl benzene sulfonate, disodium octyl sulfosuccinate, sodium butyl naphthalene sulfonate, ethoxylated sodium lauryl sulfosuccinate, sodium stearate, and sodium lauroyl sarcoside, or a mixture of two or more. Examples of anionic surfactants are also mentioned in WO 2007/076337 (see page 7, line 8 to page 9, line 3—which is hereby incorporated by reference).

Non-Ionic Surfactants

The surfactant system may contain a non-ionic surfactant. The nonionic surfactant may preferably be a water insoluble nonionic surfactant or a water soluble nonionic surfactant, or mixtures thereof. Examples of suitable nonionic surfactants are given below.

Examples of suitable water insoluble nonionic surfactants include alkyl and aryl: glycerol ethers, glycol ethers, ethanolamides, sulfoanylamides, alcohols, amides, alcohol ethoxylates, glycerol esters, glycol esters, ethoxylates of glycerol ester and glycol esters, sugar-based alkyl polyglycosides, polyoxyethylenated fatty acids, alkanolamine condensates, alkanolamides, tertiary acetylenic glycols, polyoxyethylenated mercaptans, carboxylic acid esters, and polyoxyethylenated polyoxyproylene glycols. Also included are EO/PO block copolymers (EO is ethylene oxide, PO is propylene oxide), EO polymers and copolymers, polyamines, and polyvinylpynolidones.

Water soluble nonionic surfactants typically have a higher ethylene oxide content in the hydrophilic region of the surfactant in comparison to water insoluble nonionic surfactants.

In an embodiment the water soluble nonionic surfactant is a linear primary, or secondary or branched alcohol ethoxylate having the formula: $RO(CH_2CH_2O)_nH$, wherein R is the hydrocarbon chain length and n is the average number of moles of ethylene oxide. In a preferred embodiment R is linear primary or branched secondary hydrocarbon chain length in the range from C9 to C16 and n ranges from 6 to 13. Especially preferred is the alcohol ethoxylate where R is linear C9-C11 hydrocarbon chain length, and n is 6.

Examples of commercially available water soluble nonionic alcohol ethoxylate surfactants include NEODOL™ 91-6, TOMADOL™ 91-6, or BIO-SOFT™ N23-6.5.

Examples of non-ionic surfactants are also mentioned in WO 2007/076337 (see page 9, line 5 to page 12, line 14—which is hereby incorporated by reference).

Examples of specific carpet cleaner compositions are disclosed in Examples 10 and 11 below. Any bacteria culture of the invention, or combinations thereof, may be used. However, in a preferred embodiment the bacteria cultures used are PTA-7548 and PTA-7547. The ratio between the two cultures may be between 1:10 to 10:1, preferably 1:2 to 2:1, such as around 1:1.

The bacterial culture(s) of the invention should be present in the cleaning composition, such as carpet cleaners, in effective amounts. Effective amounts can easily be determined by one skilled in the art.

Salts and Buffer Salts

The cleaning composition may contain one or more salts and/or buffer salts. The salts or buffer salts may be any known inorganic salt, but is preferably a salt selected from the group consisting of alkali metal salts of nitrates, acetates, chlorides, bromides, iodides, sulfates, hydroxides, carbonates, hydrogen carbonates, (also called bicarbonates), phosphates, sulfides, and sulfites; ammonium salts of nitrates, acetates, chlorides, bromides, iodides, sulfates, hydroxides, carbonates, hydrogen carbonates (also called bicarbonates), phosphates, sulfides, and sulfites; alkaline earth metal salts of nitrates, chlorides, bromides, iodides, sulfates, sulfides, and hydrogen carbonates; manganese, iron, copper, and zinc salts of nitrates, acetates, chlorides, bromides, iodides, and sulfates; citrates and borates.

Especially contemplated are carbonates or bicarbonates, in particular selected from the group consisting of sodium carbonate and sodium bicarbonate, or a mixture thereof. In a specific embodiment the ratio between sodium carbonate and sodium bicarbonate is between 1:10 to 10:1.

The total amount of salts and/or buffer salts is preferably between 0.8 to 8 wt. %, preferably 1-5 wt. %, more preferably around 2 wt. % of the final in-use cleaning composition.

Enzymes

One or more enzyme activities may be present in a composition of the invention and when practicing a method of the invention. Especially contemplated enzymes include proteases, alpha-amylases, cellulases, lipases, peroxidases/oxidases, pectate lyases, and mannanases, or mixtures thereof.

Proteases:

Suitable proteases include those of animal, vegetable or microbial origin. Microbial origin is preferred. Chemically modified or protein engineered mutants are included. The protease may be a serine protease or a metallo protease, preferably an alkaline microbial protease or a trypsin-like protease. Examples of alkaline proteases are subtilisins, especially those derived from *Bacillus*, e.g., subtilisin Novo, subtilisin Carlsberg, subtilisin 309, subtilisin 147 and subtilisin 168 (described in WO 89/06279). Examples of trypsin-like proteases are trypsin (e.g. of porcine or bovine origin) and the *Fusarium* protease described in WO 89/06270 and WO 94/25583.

Examples of useful proteases are the variants described in WO 92/19729, WO 98/20115, WO 98/20116, and WO 98/34946, especially the variants with substitutions in one or more of the following positions: 27, 36, 57, 76, 87, 97, 101, 104, 120, 123, 167, 170, 194, 206, 218, 222, 224, 235 and 274. Preferred commercially available protease enzymes include ALCALASE™, SAVINASE™, PRIMASE™, DURALASE™, DYRAZYM™, ESPERASE™, EVERLASE™, POLARZYME™, KANNASE™, LIQUANASE™ (Novozymes A/S), MAXATASET™, MAXACAL™, MAXAPEM™, PROPERASE™, PURAFECT™, PURAFECT OXP™, FN2™, and FN3™ (Genencor International Inc.).

Lipases:

Suitable lipases include those of bacterial or fungal origin. Chemically modified or protein engineered mutants are included. Examples of useful lipases include lipases from *Humicola* (synonym *Thermomyces*), e.g., from *H. lanuginosa* (*T. lanuginosus*) as described in EP 258 068 and EP 305 216 or from *H. insolens* as described in WO 96/13580, a *Pseudomonas* lipase, e.g. from *P. alcaligenes* or *P. pseudoalcaligenes* (EP 218 272), *P. cepacia* (EP 331 376), *P. stutzeri* (GB 1,372,034), *P. fluorescens*, *Pseudomonas* sp. strain SD 705 (WO 95/06720 and WO 96/27002), *P. wisconsinensis* (WO 96/12012), a *Bacillus* lipase, e.g. from *B. subtilis* (Dartois et al. (1993), Biochemica et Biophysica Acta, 1131, 253-360), *B. stearothermophilus* (JP 64/744992) or *B. pumilus* (WO 91/16422).

Other examples are lipase variants such as those described in WO 92/05249, WO 94/01541, EP 407 225, EP 260 105, WO 95/35381, WO 96/00292, WO 95/30744, WO 94/25578, WO 95/14783, WO 95/22615, WO 97/04079 and WO 97/07202.

Preferred commercially available lipase enzymes include LIPOLASE™ AND LIPOLASE ULTRA™, or LIPEX™ (Novozymes A/S).

Cutinase:

The method of the invention may be carried out in the presence of cutinase. classified in EC 3.1.1.74.

The cutinase used according to the invention may be of any origin. Preferably cutinases are of microbial origin, in particular of bacterial, of fungal or of yeast origin.

Cutinases are enzymes which are able to degrade cutin. In a preferred embodiment, the cutinase is derived from a strain of *Aspergillus*, in particular *Aspergillus oryzae*, a strain of *Alternaria*, in particular *Alternaria brassiciola*, a strain of *Fusarium*, in particular *Fusarium solani, Fusarium solani pisi, Fusarium roseum culmorum*, or *Fusarium roseum sambucium*, a strain of *Helminthosporum*, in particular *Helminthosporum sativum*, a strain of *Humicola*, in particular *Humicola insolens*, a strain of *Pseudomonas*, in particular *Pseudomonas mendocina*, or *Pseudomonas putida*, a strain of *Rhizoctonia*, in particular *Rhizoctonia solani*, a strain of *Streptomyces*, in particular *Streptomyces scabies*, or a strain of *Ulocladium*, in particular *Ulocladium consortiale*. In a most preferred embodiment the cutinase is derived from a strain of *Humicola insolens*, in particular the strain *Humicola insolens* DSM 1800. *Humicola insolens* cutinase is described in WO 96/13580 which is herby incorporated by reference. The cutinase may be a variant, such as one of the variants disclosed in WO 00/34450 and WO 01/92502, which are hereby incorporated by reference. Preferred cutinase variants include variants listed in Example 2 of WO 01/92502, which is hereby specifically incorporated by reference.

Preferred commercial cutinases include NOVOZYM™ 51032 (available from Novozymes A/S, Denmark).

The method of the invention may be carried out in the presence of phospholipase classified as EC 3.1.1.4 and/or EC 3.1.1.32. As used herein, the term phospholipase is an enzyme which has activity towards phospholipids. Phospholipids, such as lecithin or phosphatidylcholine, consist of glycerol esterified with two fatty acids in an outer (sn-1) and the middle (sn-2) positions and esterified with phosphoric acid in the third position; the phosphoric acid, in turn, may be esterified to an amino-alcohol. Phospholipases are enzymes which participate in the hydrolysis of phospholipids. Several types of phospholipase activity can be distinguished, including phospholipases $A_1$ and $A_2$ which hydrolyze one fatty acyl group (in the sn-1 and sn-2 position, respectively) to form lysophospholipid; and lysophospholipase (or phospholipase B) which can hydrolyze the remaining fatty acyl group in lysophospholipid. Phospholipase C and phospholipase D (phosphodiesterases) release diacyl glycerol or phosphatidic acid respectively.

The term phospholipase includes enzymes with phospholipase activity, e.g., phospholipase A ($A_1$ or $A_2$), phospholipase B activity, phospholipase C activity or phospholipase D activity. The term "phospholipase A" used herein in connection with an enzyme of the invention is intended to cover an enzyme with Phospholipase $A_1$ and/or Phospholipase $A_2$ activity. The phospholipase activity may be provided by enzymes having other activities as well, such as, e.g., a lipase with phospholipase activity. The phospholipase activity may, e.g., be from a lipase with phospholipase side activity. In other embodiments of the invention the phospholipase enzyme activity is provided by an enzyme having essentially only phospholipase activity and wherein the phospholipase enzyme activity is not a side activity.

The phospholipase may be of any origin, e.g., of animal origin (such as, e.g., mammalian), e.g. from pancreas (e.g., bovine or porcine pancreas), or snake venom or bee venom. Preferably the phospholipase may be of microbial origin, e.g., from filamentous fungi, yeast or bacteria, such as the genus or species *Aspergillus*, e.g., *A. niger*; *Dictyostelium*, e.g., *D. discoideum*; *Mucor*, e.g. *M. javanicus, M. mucedo, M. subtilissimus*; *Neurospora*, e.g. *N. crassa*; *Rhizomucor*, e.g., *R. pusillus*; *Rhizopus*, e.g. *R. arrhizus, R. japonicus, R. stolonifer*; *Sclerotinia*, e.g., *S. libertiana*; *Trichophyton*, e.g. *T. rubrum*; *Whetzelinia*, e.g., *W. sclerotiorum*; *Bacillus*, e.g., *B. megaterium, B. subtilis*; *Citrobacter*, e.g., *C. freundii*; *Enterobacter*, e.g., *E. aerogenes, E. cloacae Edwardsiella, E. tarda*; *Erwinia*, e.g., *E. herbicola*; *Escherichia*, e.g., *E. coli*; *Klebsiella*, e.g., *K. pneumoniae*; *Proteus*, e.g., *P. vulgaris*; *Providencia*, e.g., *P. stuartii*; *Salmonella*, e.g. *S. typhimurium*; *Serratia*, e.g., *S. liquefasciens, S. marcescens*; *Shigella*, e.g., *S. flexneri*; *Streptomyces*, e.g., *S. violeceoruber*; *Yersinia*, e.g., *Y. enterocolitica*. Thus, the phospholipase may be fungal, e.g., from the class *Pyrenomycetes*, such as the genus *Fusarium*, such as a strain of *F. culmorum, F. heterosporum, F. solani*, or a strain of *F. oxysporum*. The phospholipase may also be from a filamentous fungus strain within the genus *Aspergillus*, such as a strain of *Aspergillus awamori, Aspergillus foetidus, Aspergillus japonicus, Aspergillus niger* or *Aspergillus oryzae*.

Preferred phospholipases are derived from a strain of *Humicola*, especially *Humicola lanuginosa*. The phospholipase may be a variant, such as one of the variants disclosed in WO 00/32758, which are hereby incorporated by reference. Preferred phospholipase variants include variants listed in Example 5 of WO 00/32758, which is hereby specifically incorporated by reference. In another preferred embodiment the phospholipase is one described in WO 04/111216, especially the variants listed in the table in Example 1.

In another preferred embodiment the phospholipase is derived from a strain of *Fusarium*, especially *Fusarium oxysporum*. The phospholipase may be the one concerned in WO 98/026057 displayed in SEQ ID NO: 2 derived from *Fusarium oxysporum* DSM 2672, or variants thereof.

In a preferred embodiment of the invention the phospholipase is a phospholipase $A_1$ (EC. 3.1.1.32). In another preferred embodiment of the invention the phospholipase is a phospholipase $A_2$ (EC.3.1.1.4.).

Examples of commercial phospholipases include LECITASE™ and LECITASE™ ULTRA, YIELSMAX, or LIPOPAN F (available from Novozymes A/S, Denmark).

Amylases:

Suitable amylases (alpha and/or beta) include those of bacterial or fungal origin. Chemically modified or protein engineered mutants are included. Amylases include, for example, alpha-amylases obtained from *Bacillus*, e.g. a special strain of *B. licheniformis*, described in more detail in GB 1,296,839, or the *Bacillus* sp. strains disclosed in WO 95/026397 or WO 00/060060.

Examples of useful amylases are the variants described in WO 94/02597, WO 94/18314, WO 96/23873, WO 97/43424, WO 01/066712, WO 02/010355, WO 02/031124 and WO 2006/002643 (which references all incorporated by reference.

Commercially available amylases are DURAMYL™, TERMAMYL™, TERMAMYL ULTRA™, NATALASE™, STAINZYME™, FUNGAMYL™ and BAN™ (Novozymes A/S), RAPIDASE™ and PURASTAR™ (from Genencor International Inc.).

Cellulases:

Suitable cellulases include those of bacterial or fungal origin.

Chemically modified or protein engineered mutants are included. Suitable cellulases include cellulases from the genera *Bacillus, Pseudomonas, Humicola, Fusarium, Thielavia, Acremonium*, e.g. the fungal cellulases produced from *Humicola insolens, Thielavia terrestris, Myceliophthora thermophila*, and *Fusarium oxysporum* disclosed in U.S. Pat. No. 4,435,307, U.S. Pat. No. 5,648,263, U.S. Pat. No. 5,691,178, U.S. Pat. No. 5,776,757, WO 89/09259, WO 96/029397, and WO 98/012307.

Especially suitable cellulases are the alkaline or neutral cellulases having color care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. No. 5,457,046, U.S. Pat. No. 5,686,593, U.S. Pat. No. 5,763,254, WO 95/24471, WO 98/12307 and PCT/DK98/00299.

Commercially available cellulases include CELLUZYME™, CAREZYME™, ENDOLASE™, RENOZYME™ (Novozymes A/S), CLAZINASE™ and PURADAX HA™ (Genencor International Inc.), and KAC-500(B)™ (Kao Corporation).

Peroxidases/Oxidases: Suitable peroxidases/oxidases include those of plant, bacterial or fungal origin. Chemically modified or protein engineered mutants are included. Examples of useful peroxidases include peroxidases from *Coprinus*, e.g. from *C. cinereus*, and variants thereof as those described in WO 93/24618, WO 95/10602, and WO 98/15257.

Commercially available peroxidases include GUARDZYME™ and NOVOZYM™ 51004 (Novozymes A/S).

Pectate Lyases (Also Called Polygalacturonate Lyases):

Examples of pectate lyases include pectate lyases that have been cloned from different bacterial genera such as *Erwinia, Pseudomonas, Klebsiella* and *Xanthomonas*, as well as from *Bacillus subtilis* (Nasser et al. (1993) FEBS Letts. 335:319-326) and *Bacillus* sp. YA-14 (Kim et al. (1994) Biosci. Biotech. Biochem. 58:947-949). Purification of pectate lyases with maximum activity in the pH range of 8-10 produced by *Bacillus pumilus* (Dave and Vaughn (1971) J. Bacteriol. 108: 166-174), *B. polymyxa* (Nagel and Vaughn (1961) Arch. Biochem. Biophys. 93:344-352), *B. stearothermophilus* (Karbassi and Vaughn (1980) Can. J. Microbiol. 26:377-384), *Bacillus* sp. (Hasegawa and Nagel (1966) J. Food Sci. 31:838-845) and *Bacillus* sp. RK9 (Kelly and Fogarty (1978) Can. J. Microbiol. 24:1164-1172) have also been described. Any of the above, as well as divalent cation-independent and/or thermostable pectate lyases, may be used in practicing the invention. In preferred embodiments, the pectate lyase comprises the amino acid sequence of a pectate lyase disclosed in Heffron et al., (1995) Mol. Plant-Microbe Interact. 8: 331-334 and Henrissat et al., (1995) Plant Physiol. 107: 963-976. Specifically contemplated pectate lyases are disclosed in WO 99/27083 and WO 99/27084. Other specifically contemplated pectate lyases derived from *Bacillus licheniformis* is disclosed as SEQ ID NO: 2 in U.S. Pat. No. 6,284,524 (which document is hereby incorporated by reference). Specifically contemplated pectate lyase variants are disclosed in WO 02/006442, especially the variants disclosed in the Examples in WO 02/006442 (which document is hereby incorporated by reference).

Examples of commercially available alkaline pectate lyases include BIOPREP™ and SCOURZYME™ L from Novozymes A/S, Denmark.

Mannanase:

Examples of mannanases (EC 3.2.1.78) include mannanases of bacterial and fungal origin. In a specific embodiment the mannanase is derived from a strain of the filamentous fungus genus *Aspergillus*, preferably *Aspergillus niger* or *Aspergillus aculeatus* (WO 94/25576). WO 93/24622 discloses a mannanase isolated from *Trichoderma reseei*. Mannanases have also been isolated from several bacteria, including *Bacillus* organisms. For example, Talbot et al., Appl. Environ. Microbiol., Vol. 56, No. 11, pp. 3505-3510 (1990) describes a beta-mannanase derived from *Bacillus stearothermophilus*. Mendoza et al., World J. Microbiol. Biotech., Vol. 10, No. 5, pp. 551-555 (1994) describes a beta-mannanase derived from *Bacillus subtilis*. JP-A-03047076 discloses a beta-mannanase derived from *Bacillus* sp. JP-A-63056289 describes the production of an alkaline, thermostable beta-mannanase. JP-A-63036775 relates to the *Bacillus* microorganism FERM P-8856 which produces beta-mannanase and beta-mannosidase. JP-A-08051975 discloses alkaline beta-mannanases from alkalophilic *Bacillus* sp. AM-001. A purified mannanase from *Bacillus amyloliquefaciens* is disclosed in WO 97/11164. WO 91/18974 describes a hemicellulase such as a glucanase, xylanase or mannanase active. Contemplated are the alkaline family 5 and 26 mannanases derived from *Bacillus agaradhaerens, Bacillus licheniformis, Bacillus halodurans, Bacillus clausii, Bacillus* sp., and *Humicola insolens* disclosed in WO 99/64619. Especially contemplated are the *Bacillus* sp. mannanases concerned in the Examples in WO 99/64619 which document is hereby incorporated by reference.

Examples of commercially available mannanases include MANNAWAY™ available from Novozymes A/S Denmark.

The enzyme(s) may be present in a composition of the invention is an amount from 0.1-10 wt-%, preferably 0.5-5 wt-%, especially 1-2 wt-% of the composition.

Method of the Invention

In the third aspect the invention relates to methods of washing laundry or fabrics comprising subjecting said laundry or fabric to a composition or bacteria culture of the invention.

The method of the invention may be carried as out by adding a composition or bacteria culture of the invention to washing liquor, which may or may not contain the laundry or fabric to be washed. It is important to insure proper conditions during washing or cleaning to allow the bacteria culture in question to degrade the soils/stains in question. In case dormant bacteria spores are used suitable conditions and/or ingredients for germination may be required. It is important to understand that the storage condition for bacteria cultures or compositions of the invention may be different from in-use conditions.

A method of washing laundry or fabric or cleaning surfaces of the invention may be carried out as a one-step method or a two-step method. The treatment steps may be carried out simultaneously or sequentially. In one embodiment treatment is carried out using a culture and one or more active ingredients (as described above) simultaneously. According to the invention laundry or fabric may be treated with a bacteria culture of the invention and one or more active ingredients sequentially in one or two baths. In an embodiment the method of the invention may be carried out in two steps, i.e., by first treating the laundry, fabric or surface in question with a bacteria culture of the invention and subsequently or simultaneously with an active ingredient, especially enzyme, e.g., a protease, alpha-amylase, cellulase, lipase, peroxidases/oxidase, pectate lyase, and mannanase, or mixtures thereof. A two step method of the invention may be carried out in one bath or sequentially in two (separate) baths.

The bacterial culture or composition of the invention is used in an effective concentration during a method of the invention. In an embodiment the concentration of bacteria culture during washing may be in the range from $1\times10^6$ to $1\times10^{12}$ bacteria cells per L wash liquor, preferably above $1\times10^7$ bacteria cells per L wash liquor.

The pH during washing may be in the range from 5-11. The temperature may typically be in the range from 10-90° C., preferably 20-50° C. In an embodiment washing is carried out for a period between 1 and 1440 minutes. The fabric:wash liquor ratio may preferably in the range from 1:1 to 1:20, preferably 1:10. As mentioned above one or more enzymes may be present during washing. Contemplated enzymes include any of the ones mentioned in the "Enzymes" section above, which include proteases, alpha-amylases, cellulases, lipases, peroxidase/oxidase, mannanases, pectate lyases, or a mixture thereof. Enzymes may be present in an amount corresponding to 0.01-100 mg of enzyme protein per liter of wash liquor, preferably 0.05-5 mg of enzyme protein per liter of wash liquor, in particular 0.1-1 mg of enzyme protein per liter of wash liquor. In a preferred embodiment the laundry or fabric is rinsed after washing.

Laundry and/or Fabrics

When using the term "fabrics" it encompasses all kind of fabrics, textiles, fibers, clothes garments and the like. "Laundry" is, in contrast to "newly manufactured fabrics", already used and/or stained/soiled clothes in need of washing. Washing laundry is typically carried out in private households, while washing newly manufactured fabrics are mainly done in the textile industry. Washing of laundry can also occur in commercial and institutional facilities such as hospitals, prisons, uniform service companies, and the like. The fabric or laundry may be made from any suitable material. In preferred embodiments the fabrics and/or laundry are made from cellulosic materials, synthetic materials and/or man-made fibers, or blends thereof.

Examples of contemplated cellulosic materials include cotton, viscose, rayon, ramie, linen, lyocell (e.g., TENCEL™, produced by Courtaulds Fibers), or blends thereof, or blends of any of these fibers together with synthetic or man-made fibers (e.g., polyester, polyamid, nylon) or other natural fibers such as wool and silk, such as viscose/cotton blends, lyocell/cotton blends, viscose/wool blends, lyocell/wool blends, cotton/wool blends; flax (linen), ramie and other fabrics and/or laundry based on cellulose fibers, including all blends of cellulosic fibers with other fibers such as wool, polyamide, acrylic and polyester fibers, e.g., viscose/cotton/polyester blends, wool/cotton/polyester blends, flax/cotton blends etc. The fabric and/or laundry may also be a synthetic materials, e.g., consisting of essentially 100% polyester, polyamid, nylon, respectively. The term "wool," means any commercially useful animal hair product, for example, wool from sheep, camel, rabbit, goat, llama, and known as merino wool, Shetland wool, cashmere wool, alpaca wool, mohair etc. and includes wool fibers and animal hair. The method of the invention can be used on wool or animal hair material in the form of top, fiber, yarn, or woven or knitted fabrics.

A Method of Cleaning Surfaces

A composition or bacteria culture of the invention may also be used for cleaning surfaces including hard and soft surfaces.

Thus, in a fourth aspect the invention relates to a method of cleaning a surface comprising subjecting said surface to a composition or bacterial culture of the invention.

Examples of contemplated hard surfaces are concrete, metal, glass, ceramic, plastic, linoleum and similar surfaces. Hard surfaces are typically found in toilets, shower stalls, bathtubs, sinks, countertops, walls, floors and also include road surfaces.

Examples of contemplated soft surfaces include carpet, furniture, upholstery fabric, slippers, clothing and other fibrous material surfaces.

It should be mentioned that compositions or bacterial cultures of the invention are also contemplated for cleaning objects such as drains or outlet pipes for waster water, sewers from, e.g., homes or industrial enterprises, vehicles, holding tanks, septic tanks etc. It is also contemplated using compositions or bacteria cultures of the invention for degrading, e.g., organic waste materials.

In a specifically contemplated embodiment the invention relates to a method of cleaning carpets or other fibrous material surfaces.

It is to be understood that carpet cleaning cleans the carpet, but may also prevent or control odors from, e.g., organic spills, such as food and the like.

The odor control may be preventive or precautionary, i.e., added to the carpet, e.g., during manufacture of the carpet or fibrous material in question or after installation of a new carpet, or may also be used for, e.g., spot cleaning or full scale cleaning of soiled carpet or fibrous materials.

In a preferred embodiment of the invention the composition or culture for cleaning surfaces, such as soft surfaces, especially carpets and other fibrous material, comprise the following strains alone or in combination: PTA-7548 and PTA-7547. The ratio between the two cultures may be between 1:10 to 10:1, preferably 1:2 to 2:1, such as around 1:1.

The invention also relates to a method of preventing and/or controlling odor caused by organic material spilled on carpet or other fibrous material, comprising applying a bacteria culture of the invention or a composition of the invention to the carpet before and/or after spill of organic material on the carpet or other fibrous material. The bacteria culture is applied to the carpet at a concentration of between $10^5$ and $10^9$, preferably between $10^6$ and $10^8$ cells per gram of carpet fiber, especially $10^7$ cells per grams of carpet fibers.

Use of Bacteria Culture of the Invention

In the final aspect, the invention relates to the use of a composition or bacteria culture of the invention for cleaning or washing fabric and/or soft or hard surfaces. It is also contemplated to use compositions or bacteria cultures of the invention for degrading, e.g., organic waste materials. In a preferred embodiment a bacteria culture of the invention or a combination thereof, especially PTA-7548 and PTA-7547, are used in a carpet cleaner composition, especially one disclosed in WO2007/076337 (which is hereby incorporated by reference).

The carpet cleaner may be a carpet extraction cleaner or a carpet spot cleaner. Examples of such carpet cleaners are disclosed in Examples 10 and 11 below. In a preferred embodiment the bacteria cultures used in the carpet cleaners are PTA-7548 and/or PTA-7547. It should be understood that the bacteria culture(s) should be present in effective amounts. Effective amounts can easily be determined by one skilled in the art.

Materials & Methods

Deposit of Biological Material

The following biological material has been deposited under the terms of the Budapest Treaty at American Type Culture Collection (ATCC), 10801 University Blvd., Manassas, Va. 20108, USA, and given the following accession number:

| Identification | Accession Number | Date of Deposit |
|---|---|---|
| Bacillus amyloliquefaciens | PTA-7541 | 20 Apr. 2006 |
| Bacillus amyloliquefaciens | PTA-7542 | 20 Apr. 2006 |
| Bacillus atrophaeus | PTA-7543 | 20 Apr. 2006 |
| Bacillus amyloliquefaciens | PTA-7544 | 20 Apr. 2006 |
| Bacillus amyloliquefaciens | PTA-7545 | 20 Apr. 2006 |
| Bacillus amyloliquefaciens | PTA-7546 | 20 Apr. 2006 |
| Bacillus subtilis subsp. Subtilis | PTA-7547 | 20 Apr. 2006 |
| Bacillus velezensis | PTA-7548 | 20 Apr. 2006 |
| Bacillus amyloiquefaciens | PTA-7549 | 20 Apr. 2006 |
| Bacillus simplex | PTA-7550 | 20 Apr. 2006 |
| Bacillus simplex | PTA-7789 | 18 Aug. 2006 |
| Bacillus amyloliquefaciens | PTA-7790 | 18 Aug. 2006 |
| Bacillus amyloliquefaciens | PTA-7791 | 18 Aug. 2006 |
| Bacillus atrophaeus | PTA-7792 | 18 Aug. 2006 |
| Bacillus amyloliquefaciens | PTA-7793 | 18 Aug. 2006 |

The strain has been deposited under conditions that assure that access to the culture will be available during the pendency of this patent application to one determined by the Commissioner of Patents and Trademarks to be entitled thereto under 37 C.F.R. §1.14 and 35 U.S.C. §122. The deposit represents a pure culture of the deposited strain. The deposit is available as required by foreign patent laws in countries wherein counterparts of the subject application or its progeny are filed. However, it should be understood that the availability of a deposit does not constitute a license to practice the subject invention in derogation of patent rights granted by governmental action.

Fabrics:

All fabrics were purchased from Tesffabrics, Inc., West Pittson, Pa. 18643, USA

| Fabric | Catalog Number |
|---|---|
| Ground in clay on cotton | STC GC C |
| Synthetic Sebum on cotton | STC SS DSC |
| Ballast soil | C-S-31 |
| cotton soiled with aged blood | C-S-01 |
| cotton soiled with butterfat and colorant | C-S-10 |
| cotton soiled with oil, <60° C. | C-09 |
| soiled cotton with used motor oil | W-10-GM |

Fabric in Example 9 was obtained from Warwick Equest:
WARWICK EQUEST LIMITED
Unit 55, Consett Business Park
Consett, County Durham
DH8 6BN
ENGLAND Media and Reagents:

Chemicals used as buffers and substrates were commercial products of at least reagent grade.
PCB (Plate Count Broth) purchased from Difco, Franklin Lakes, N.J., USA.
LB (Luria-Bertani Broth) purchased from Difco, Franklin Lakes, N.J., USA.

| | |
|---|---|
| 10D | Sebum and particulates (carbon black) |
| AS 12 | Composite general soil (oil, milk protein, particulates) |
| CS 62 | Pork lard stained with sudan red |

Hamburger grease stained with Macrolex Violet Dye.
Equipment
Spectrophotometer: Gretag-Macbeth Color Eye 7000A
Methods
Fabric Stain Cleaning Procedure An overnight culture of bacteria is grown in 10 ml in a complex nutrient rich media like PCB or LB at 35° C. with shaking at 250 rpm. Any culture that does not reach a minimal $OD_{600}$ of 1.0 is re-inoculated at a later date and not used. $SSC_3$ Minimal Media is used according to the following recipe:

Base Media (all values in g/L unless otherwise noted)

| | |
|---|---|
| $NH_4Cl$ | 0.8 |
| $MgSO_4$ | 0.2 |
| $CaCl_2 \cdot 2H_2O$ | 0.01 |
| $FeCl_3$ | 0.005 |
| $KH_2PO_4$ | 0.15 |
| Trace Minerals | 1 ml/L |
| Glucose | 2.0 |
| MOPS | 5.1 | pH to 8.0

1000× Trace Minerals (all values in mg/L)

| | |
|---|---|
| $FeSO_4 \cdot 7H_2O$ | 28 |
| $ZnSO_4 \cdot 7H_2O$ | 140 |
| $MnSO_4 \cdot H_2O$ | 84 |
| $CoCl_2 \cdot 6H_2O$ | 24 |
| $CuSO_4 \cdot 5H_2O$ | 25 |
| $NaMoO_4 \cdot 2H_2O$ | 24 |

Microtiter plates containing punched stained fabrics are used as is. 200 microliters of sterile SSC is added to every well.

5 microliters of the overnight culture is inoculated into the 200 microliters of $SSC_3$ containing 0.2% glucose (w/v) that is added in the previous step. Plate is grown with shaking at 35° C. for 48 hours. After growth, wells are rinsed with DI water 3×, then the fabric is dried overnight in a 35° C. incubator for photography For shake flask studies:

10 ml overnight cultures of strains are grown in PCB at 35° C. with shaking at 200 rpm. The next day, 0.25 ml of this culture is used to inoculate 10 ml of $SSC_3$ containing 0.2% glucose. This minimal media culture is also grown overnight at 35° C. with shaking at 200 rpm.

0.5 ml of this overnight culture is used to inoculate 150 ml of each $SSC_3$ culture+stain fabric. Negative controls containing stained fabric will be used containing 0.005% (w/v) myacide to inhibit all bacterial growth. Control fabric samples will be treated identically to experimental samples. All culture flasks will be grown for 48 hours at 35° C. with shaking at 200 rpm.

Fabric samples are removed, rinsed with distilled water and analyzed for reflective analysis on Gretag-Macbeth Color Eye 7000A spectrophotometer. The deltaE value is determined.

EXAMPLES

Example 1

Cleaning of Blood Stained Cotton Fabric

The following *Bacillus* strains deposited at ATCC were tested following the "Fabric stain cleaning procedure" described in the "Methods & Methods"-section on cotton fabric soiled with aged blood (Testfabrics Inc., PA, USA).

| Strains: | Identification | DeltaE |
|---|---|---|
| | Cotton (control) | 41.7 |
| PTA-7547 | Bacillus subtilis | 22.81 |
| PTA-7542 | Bacillus amyloliquefaciens | 28.32 |
| PTA-7550 | Bacillus simplex | 27.02 |
| PTA-7548 | Bacillus velezensis | 33.84 |
| PTA-7543 | Bacillus atrophaeus | 23.92 |
| PTA-7544 | Bacillus amyloliquefaciens | 20.67 |
| PTA-7545 | Bacillus amyloliquefaciens | 23.87 |
| PTA-7546 | Bacillus amyloliquefaciens | 17.99 |
| PTA-7549 | Bacillus amyloliquefaciens | 30.75 |

Example 2

Cleaning of Cotton Fabric with Ballast Stains

The following *Bacillus* strains deposited at ATCC were tested following the "Fabric stain cleaning procedure" described in the "Methods & Methods"-section on ballast soiled cotton fabric (Testfabrics Inc., PA, USA).

| Strains: | Identification | DeltaE |
|---|---|---|
| | Cotton (Control) | 20.3 |
| PTA-7547 | Bacillus subtilis | 18.29 |
| PTA-7542 | Bacillus amyloliquefaciens | 13.49 |
| PTA-7550 | Bacillus simplex | 13.34 |
| PTA-7543 | Bacillus atrophaeus | 11.17 |
| PTA-7545 | Bacillus amyloliquefaciens | 9.78 |
| PTA-7546 | Bacillus amyloliquefaciens | 12.17 |
| PTA-7549 | Bacillus amyloliquefaciens | 14.98 |
| PTA-7792 | Bacillus atrophaeus | 16.51 |
| PTA-7793 | Bacillus amyloliquefaciens | 6.51 |

Example 3

Cleaning of Butterfat Soiled Cotton Fabric

The following *Bacillus* strains deposited at ATCC were tested following the "Fabric stain cleaning procedure" described in the "Methods & Methods"-section on butterfat soiled cotton fabric (Testfabrics Inc., PA, USA).

| Strains: | Identification | DeltaE |
|---|---|---|
| | Cotton (Control) | 15.7 |
| PTA-7547 | Bacillus subtilis | 4.12 |
| PTA-7542 | Bacillus amyloliquefaciens | |
| PTA-7548 | Bacillus velezensis | 4.87 |
| PTA-7546 | Bacillus amyloliquefaciens | 5.45 |
| PTA-7549 | Bacillus amyloliquefaciens | 4.63 |

Example 4

Cleaning of Cooking Oil Soiled Cotton Fabric

The following *Bacillus* strains deposited at ATCC were tested following the "Fabric stain cleaning procedure" described in the "Methods & Methods"-section on cooking oil soiled cotton fabric (Testfabrics Inc., PA, USA).

| Key Strains: | Identification | DeltaE |
|---|---|---|
| | Cotton (Control) | 18.7 |
| PTA-7547 | *Bacillus subtilis* | 5.15 |
| PTA-7543 | *Bacillus atrophaeus* | 4.82 |
| PTA-7544 | *Bacillus amyloliquefaciens* | 3.26 |
| PTA-7545 | *Bacillus amyloliquefaciens* | 2.96 |
| PTA-7541 | *Bacillus amyloliquefaciens* | 3.09 |

Example 5

Cleaning of Sebum Soiled Cotton Fabric

The following *Bacillus* strains deposited at ATCC were tested following the "Fabric stain cleaning procedure" described in the "Methods & Methods"-section on sebum soiled cotton fabric (Testfabrics Inc., PA, USA).

| Key Strains: | Identification | DeltaE |
|---|---|---|
| | Cotton (Control) | 19.3 |
| PTA-7547 | *Bacillus subtilis* | 4.17 |

Example 6

Cleaning of Sebum and Particulate Soiled Cotton Fabric

The following *Bacillus* strains deposited at ATCC were tested following the "Fabric stain cleaning procedure" described in the "Methods & Methods"-section on sebum and particulate soiled cotton fabric (Testfabrics Inc., PA, USA).

| Key Strains: | Identification | DeltaE |
|---|---|---|
| | Cotton (Control) | 18.3 |
| PTA-7790 | *Bacillus amyloliquefaciens* | 2.85 |
| PTA-7792 | *Bacillus atrophaeus* | 3.47 |

Example 7

Cleaning of Composite General Soil Soiled Cotton Fabric

The following *Bacillus* strains deposited at ATCC were tested following the "Fabric stain cleaning procedure" described in the "Methods & Methods"-section on composite general soil soiled cotton fabric (Testfabrics Inc., PA, USA).

| Key Strains: | Identification | DeltaE |
|---|---|---|
| | Cotton (Control) | 18.3 |
| PTA-7790 | *Bacillus amyloliquefaciens* | 6.42 |

Example 8

Cleaning of Pork Lard Soiled Cotton Fabric

The following *Bacillus* strains deposited at ATCC were tested following the "Fabric stain cleaning procedure" described in the "Methods & Methods"-section on pork lard soiled cotton fabric (Testfabrics Inc., PA, USA).

| Key Strains: | Identification | DeltaE |
|---|---|---|
| | Cotton (Control) | 26.33 |
| PTA-7790 | *Bacillus amyloliquefaciens* | 19.36 |
| PTA-7789 | *Bacillus simplex* | 19.95 |

Example 9

Cleaning of Hamburger Grease Soiled Cotton Fabric

The following *Bacillus* strains deposited at ATCC were tested following the "Fabric stain cleaning procedure" described in the "Methods & Methods"-section on Hamburger grease soiled cotton fabric (Warwick Equest, Consett, England).

| Key Strains: | Identification | DeltaE |
|---|---|---|
| | Cotton (Control) | 21.18 |
| PTA-7793 | *Bacillus amyloliquefaciens* | 5.38 |
| PTA-7791 | *Bacillus amyloliquefaciens* | 4.18 |

Example 10

Carpet Spot Removers

In each formulation, the active Sodium Octyl Sulfonate is introduced as B10-TERGE® PAS-8S (Stepan Company), which is a solution containing 37.8% active Sodium Octyl Sulfonate. In the following examples where Sodium Octyl Sulfonate is used, the quantity of Sodium Octyl Sulfonate is given as percent actives.

A. Anionic Surfactant and Nonionic Surfactant in a Ratio of about 6:1 (Formulation A).

This formulation is a starting formulation to be used as active cleaning base in a carpet spot remover.

| Material | % By Weight | Function |
|---|---|---|
| Water | Q.S. | Solvent for all other materials |
| Sodium Octyl Sulfonate | 1.28 | Water soluble anionic surfactant, allows powdery residue |
| Tomadol 91-6 | 0.23 | Water soluble nonionic surfactant |
| Isopropyl Alcohol | 2.50 | Organic solvent to help with water-insoluble stain removal. |
| Kathon CG/ICP | 0.050 | Preservative |
| Bronopol (BIOBAN™ BP-PLUS) | 0.025 | Preservative |
| Citric Acid | 0.25 | Provide buffering pH 6-7 |
| Caustic Soda | 0.30 | pH adjustment of citric acid to pH 6-7 |
| Bacteria cultures PTA-7548 and PTA-7547 | $5.4 \times 10^8$ cfu/ml | cleaning and odor controlling ingredient |

B. 50/50 Tomadol 91-6/Tomadol 91-2.5, 1.50% Total Surfactant (Formulation B)

| Material | % By Weight |
|---|---|
| Water | Q.S. |
| Sodium Octyl Sulfonate | 1.28 |
| Tomadol 91-6 | 0.11 |
| Tomadol 91-2.5 | 0.11 |

| Material | % By Weight |
| --- | --- |
| Isopropyl Alcohol | 2.50 |
| Kathon CG/ICP | 0.050 |
| Bronopol (BIOBAN ™ BP-PLUS) | 0.025 |
| Citric Acid | 0.25 |
| Caustic Soda | 0.30 |
| Bacteria cultures PTA-7548 and PTA-7547 | $5.4 \times 10^8$ cfu/ml |

C. 30/70 Tomadol 91-6/Tomadol 91-2.5, 1.51% Total Surfactant (Formulation C)

| Material | % By Weight |
| --- | --- |
| Water | Q.S. |
| Sodium Octyl Sulfonate | 1.28 |
| Tomadol 91-6 | 0.07 |
| Tomadol 91-2.5 | 0.16 |
| Isopropyl Alcohol | 2.50 |
| Kathon CG/ICP | 0.050 |
| Bronopol (BIOBAN ™ BP-PLUS) | 0.025 |
| Citric Acid | 0.25 |
| Caustic Soda | 0.30 |
| Bacteria cultures PTA-7548 and PTA-7547 | $5.4 \times 10^8$ cfu/ml |

D. No Isopropyl Alcohol, 2.30% Total Surfactant (Formulation D)

| Material | % By Weight |
| --- | --- |
| Water | Q.S. |
| Sodium Octyl Sulfonate | 1.96 |
| Tomadol 91-6 | 0.10 |
| Tomadol 91-2.5 | 0.24 |
| Kathon CG/ICP | 0.050 |
| Bronopol (BIOBAN ™ BP-PLUS) | 0.025 |
| Citric Acid | 0.25 |
| Caustic Soda | 0.30 |
| Bacteria cultures PTA-7548 and PTA-7547 | $5.4 \times 10^8$ cfu/ml |

D1. 0/100 Tomadol 91-6/Tomadol 91-2.5, 2.31% Total Surfactant (Formulation D1)

| Material | % By Weight |
| --- | --- |
| Water | Q.S. |
| Sodium Octyl Sulfonate | 1.96 |
| Tomadol 91-2.5 | 0.35 |
| Kathon CG/ICP | 0.050 |
| Bronopol (BIOBAN ™ BP-PLUS) | 0.025 |
| Citric Acid | 0.25 |
| Caustic Soda | 0.30 |
| Bacteria cultures PTA-7548 and PTA-7547 | $5.4 \times 10^8$ cfu/ml |

E. 20/80 Tomadol 91-6/Tomadol 91-2.5, 1.60% Total Surfactant (Formulation E)

| Material | % By Weight |
| --- | --- |
| Water | Q.S. |
| Sodium Octyl Sulfonate | 1.36 |
| Tomadol 91-6 | 0.05 |
| Tomadol 91-2.5 | 0.19 |
| Kathon CG/ICP | 0.050 |
| Bronopol (BIOBAN ™ BP-PLUS) | 0.025 |
| Citric Acid | 0.25 |
| Caustic Soda | 0.30 |
| Bacteria cultures PTA-7548 and PTA-7547 | $5.4 \times 10^8$ cfu/ml |

F. 20/80 Tomadol 91-6/Tomadol 91-2.5, 1.80% Total Surfactant (Formulation F)

| Material | % By Weight |
| --- | --- |
| Water | Q.S. |
| Sodium Octyl Sulfonate | 1.53 |
| Tomadol 91-6 | 0.054 |
| Tomadol 91-2.5 | 0.216 |
| Kathon CG/ICP | 0.050 |
| Bronopol (BIOBAN ™ BP-PLUS) | 0.025 |
| Citric Acid | 0.25 |
| Caustic Soda | 0.30 |
| Bacteria cultures PTA-7548 and PTA-7547 | $5.4 \times 10^8$ cfu/ml |

G. 20/80 Tomadol 91-6/Tomadol 91-2.5, 1.90% Total Surfactant (Formulation G)

| Material | % By Weight |
| --- | --- |
| Water | Q.S. |
| Sodium Octyl Sulfonate | 1.62 |
| Tomadol 91-6 | 0.057 |
| Tomadol 91-2.5 | 0.228 |
| Kathon CG/ICP | 0.050 |
| Bronopol (BIOBAN ™ BP-PLUS) | 0.025 |
| Citric Acid | 0.25 |
| Caustic Soda | 0.30 |
| Bacteria cultures PTA-7548 and PTA-7547 | $5.4 \times 10^8$ cfu/ml |

H. 20/80 Tomadol 91-6/Tomadol 91-2.5, 2.00% Total Surfactant (Formulation H)

| Material | % By Weight |
| --- | --- |
| Water | Q.S. |
| Sodium Octyl Sulfonate | 1.70 |
| Tomadol 91-6 | 0.06 |
| Tomadol 91-2.5 | 0.24 |
| Kathon CG/ICP | 0.050 |
| Bronopol (BIOBAN ™ BP-PLUS) | 0.025 |
| Citric Acid | 0.25 |
| Caustic Soda | 0.30 |
| Bacteria cultures PTA-7548 and PTA-7547 | $5.4 \times 10^8$ cfu/ml |

Example 11

Carpet Extraction Cleaner

An aqueous cleaning composition for use in carpet extraction cleaning is described below. The cleaning compositions illustrate products that the consumer purchases and dilutes in water by adding 2 ounces (56.7 grams) to the filling tank and filling with hot water to make a total of one gallon (3.79 liters).

Five cleaning composition formulations in weight/weight percentage are given in the table below. The ratio of TOMA- DOL 91-6 to TOMADOL 91-2.5 is also given as a percentage ratio of the total content of TOMADOL 91-6 and TOMADOL 91-2.5. Note that for all of these formulations, the only change is the relative amounts of TOMADOL 91-6 and TOMADOL 91-2.5. These in-use cleaning solution are prepared by adding 6.25 g of the cleaning formulations to a bottle, and bringing the total mass to 400 g with tap water.

|  | 50/50 | 0/100 | 25/75 | 15/85 | 20/80 |
|---|---|---|---|---|---|
| Water | Q.S. | Q.S. | Q.S. | Q.S. | Q.S. |
| Sodium Octyl Sulfonate | 2.34 | 2.34 | 2.34 | 2.34 | 2.34 |
| Tomadol 91-6 | 0.96 | 0.00 | 0.48 | 0.29 | 0.38 |
| Tomadol 91-2.5 | 0.96 | 1.91 | 1.43 | 1.63 | 1.53 |
| Kathon | 0.050 | 0.050 | 0.050 | 0.050 | 0.050 |
| Bronopol | 0.025 | 0.025 | 0.025 | 0.025 | 0.025 |
| Citric Acid | 4.25 | 4.25 | 4.25 | 4.25 | 4.25 |
| Caustic Soda | 4.90 | 4.90 | 4.90 | 4.90 | 4.90 |
| Bacteria cultures PTA-7548 and PTA-7547 | $5.4 \times 10^8$ cfu/ml | $5.4 \times 10^8$ cfu/ml | $5.4 \times 10^8$ cfu/ml | $5.4 \times 10^8$ cfu/ml | $5.4 \times 10^8$ cfu/ml |

Cleaning composition formulations. The ratio of Tomadol 91-6 to Tomadol 91-2.5 is also given as a percentage ratio of the total content of Tomadol 91-6 and Tomadol 91-2.5.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

The invention claimed is:

1. A method for treating soil or stain on a surface comprising subjecting the soil or stain to one or more isolated bacterial strains selected from the group consisting of:
   the strain having the deposit accession number PTA-7541;
   the strain having the deposit accession number PTA-7542;
   the strain having the deposit accession number PTA-7543;
   the strain having the deposit accession number PTA-7544;
   the strain having the deposit accession number PTA-7545;
   the strain having the deposit accession number PTA-7546;
   the strain having the deposit accession number PTA-7547;
   the strain having the deposit accession number PTA-7548;
   the strain having the deposit accession number PTA-7549;
   the strain having the deposit accession number PTA-7550,
   the strain having the deposit accession number PTA-7789,
   the strain having the deposit accession number PTA-7790,
   the strain having the deposit accession number PTA-7791,
   the strain having the deposit accession number PTA-7792,
   the strain having the deposit accession number PTA-7793,
   or
   a mixture of two or more of the strains.

2. The method of claim 1, wherein the method further comprises subjecting the soil or stain to one or more enzymes.

3. The method of claim 2, wherein the one or more enzymes are selected from the group consisting of a protease, an alpha-amylase, a cellulase, a lipase, a peroxidase, an oxidase, a pectate lyase, a mannase, or mixtures thereof.

4. The method of claim 1, wherein the one or more bacterial strains is the strain having the deposit accession number PTA-7541.

5. The method of claim 1, wherein the one or more bacterial strains is the strain having the deposit accession number PTA-7542.

6. The method of claim 1, wherein the one or more bacterial strains is the strain having the deposit accession number PTA-7543.

7. The method of claim 1, wherein the one or more bacterial strains is the strain having the deposit accession number PTA-7544.

8. The method of claim 1, wherein the one or more bacterial strains is the strain having the deposit accession number PTA-7545.

9. The method of claim 1, wherein the one or more bacterial strains is the strain having the deposit accession number PTA-7546.

10. The method of claim 1, wherein the one or more bacterial strains is the strain having the deposit accession number PTA-7547.

11. The method of claim 1, wherein the one or more bacterial strains is the strain having the deposit accession number PTA-7548.

12. The method of claim 1, wherein the one or more bacterial strains is the strain having the deposit accession number PTA-7549.

13. The method of claim 1, wherein the one or more bacterial strains is the strain having the deposit accession number PTA-7550.

14. The method of claim 1, wherein the one or more bacterial strains is the strain having the deposit accession number PTA-7789.

15. The method of claim 1, wherein the one or more bacterial strains is the strain having the deposit accession number PTA-7790.

16. The method of claim 1, wherein the one or more bacterial strains is the strain having the deposit accession number PTA-7791.

17. The method of claim 1, wherein the one or more bacterial strains is the strain having the deposit accession number PTA-7792.

18. The method of claim 1, wherein the one or more bacterial strains is the strain having the deposit accession number PTA-7793.

19. The method of claim 1, wherein the surface is a soft surface or a hard surface.

20. The method of claim 19, wherein the soft surface is a laundry or fabric.

* * * * *